United States Patent
Li et al.

(10) Patent No.: US 7,403,810 B2
(45) Date of Patent: Jul. 22, 2008

(54) TIME RESOLVED CONTRAST-ENHANCED MR PROJECTION IMAGING OF THE CORONARY ARTERIES WITH INTRAVENOUS CONTRAST INJECTION

(75) Inventors: Debiao Li, Naperville, IL (US); Jordin D. Green, Chicago, IL (US)

(73) Assignee: Northwestern University, Evanston, IL (US)

( * ) Notice: Subject to any disclaimer, the term of this patent is extended or adjusted under 35 U.S.C. 154(b) by 603 days.

(21) Appl. No.: 10/848,950

(22) Filed: May 19, 2004

(65) Prior Publication Data

US 2005/0261574 A1 Nov. 24, 2005

(51) Int. Cl.
*A61B 5/055* (2006.01)
(52) U.S. Cl. ...................... 600/419; 600/420
(58) Field of Classification Search ................ 600/410, 600/413, 419, 420; 324/306, 307, 309
See application file for complete search history.

(56) References Cited

U.S. PATENT DOCUMENTS

| | | | | |
|---|---|---|---|---|
| 4,893,627 | A * | 1/1990 | Kehayias et al. | 424/9.3 |
| 5,256,967 | A * | 10/1993 | Foo et al. | 324/311 |
| 5,588,431 | A * | 12/1996 | Mani et al. | 600/410 |
| 6,198,959 | B1 * | 3/2001 | Wang | 600/413 |
| 7,082,326 | B2 * | 7/2006 | Johansson | 600/420 |
| 2004/0114787 | A1 * | 6/2004 | Papgeorgiou et al. | 382/128 |

OTHER PUBLICATIONS

"Coronary Arteries: Magnetization-prepared Contrast-enhanced Three-dimensional Volume-targeted Breath-hold MR Angiography," Li et al., Radiology, 219 (2001), pp. 270-277.*
"Coronary Magnetic Resonance Angiography For the Detection of Coronary Stenoses," Kim et al, N. Engl. J. Med. vol. 345, No. 26 (Dec. 27, 2001), pp. 1863-1869.
"Whole-Heart Steady-State Free Precession Coronary Artery Magnetic Resonance Angiography," Weber et al, Nag. Res. Ind., vol. 50 (2003) pp. 1223-1228.
"'Soap-Bubble' Visualization and Quantitative Analysis of 3D Coronary Magnetic Resonance Angiograms," Etienne et al, Nag. Res. In Med., vol. 48, (2002) pp. 556-666.
"Coronary Artery Imaging Using Contrast-Enhanced 3D Segmented EPI," Dashpande et al, J. of Mag. Res. Imaging, vol. 13 (2001) pp. 676-681.

(Continued)

*Primary Examiner*—Ruth S. Smith
*Assistant Examiner*—Jonathan G Cwern
(74) *Attorney, Agent, or Firm*—Schiff Hardin LLP

(57) ABSTRACT

In a method and apparatus for contrast-enhanced magnetic resonance (MR) angiography of the right coronary artery of a patient, a bolus of MR contrast agent is selected to have a size that will cause the bolus, after injection into the patient, to wash out of right coronary chambers of the heart while still enhancing MR signals from the right coronary artery. The bolus of MR contrast agent is injected into the patient, and MR signals are generated in, and MR signals are obtained from, the patient in a time window after the bolus has washed out of the right coronary chambers and still enhances MR signals in the right coronary artery. An MR image of the right coronary artery is generated using only the MR signals obtained in the time window.

20 Claims, 3 Drawing Sheets

OTHER PUBLICATIONS

"Analysis of Cardiopulmonary Transit Times at Contrast Material-enhanced MR Imaging in Patients with Heart Disease," Francois et al, Radiology, vol. 227 (2003) pp. 447-452.

"Background Suppression with Multiple Inversion Recovery Nulling: Applications to Projective Angiography," Pauly et al, Mag. Res. In Med., vol. 37, No. 6 (1997), pp. 898-905.

"Measurement of Signal Intensities in the Presence of Noise in MR Images," Henkelman, Med. Phys., vol. 12, No. 2 (1985), pp. 232-233.

"Selective Three-Dimensional Visualization of the Coronary Arterial Lumen Using Arterial Spin Tagging," Stuber et al, Mag. Res. In Med., vol. 47 (2002), pp. 322-329.

"Echo-Planar MR Imaging of Normal and Ischemic Myocardium with Gadodiamide Injection," Wendland et al, Radiology, vol. 86, (1993), pp. 532-542.

"The Use of Contrast-Enhanced Magnetic Resonance Imaging To Identify Reversible Myocardial Dysfunction," Kim et al, N. Engl. J. Med., vol. 343, No. 20 (2000), pp. 1445-1453.

"Contrast-Enhanced Coronary Artery Imaging Using 3D TrueFISP," Deshpande et al, Mag. Res. In Med. (2003).

Coronary Arteries: Breath-hold Gadolinium-Enhanced, Three-Dimensional MR Angiography, Goldfarb et al, Radiology, vol. 206 (1998), pp. 830-834.

* cited by examiner

 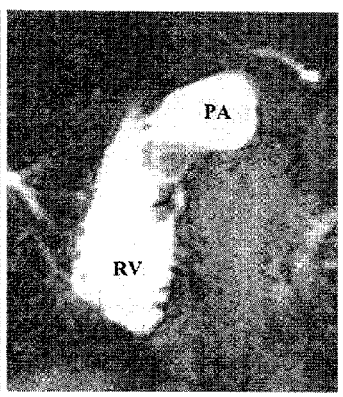 
*FIG. 3a*  *FIG. 3b*  *FIG. 3c*
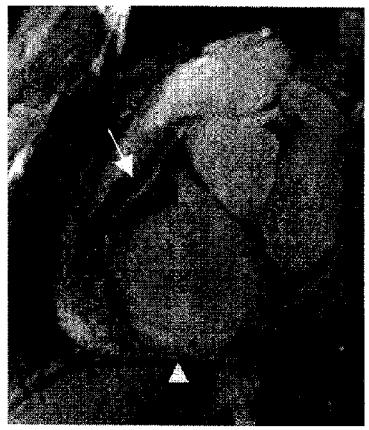 
*FIG. 4a*  *FIG. 4b*
*FIG. 5a*  *FIG. 5b*
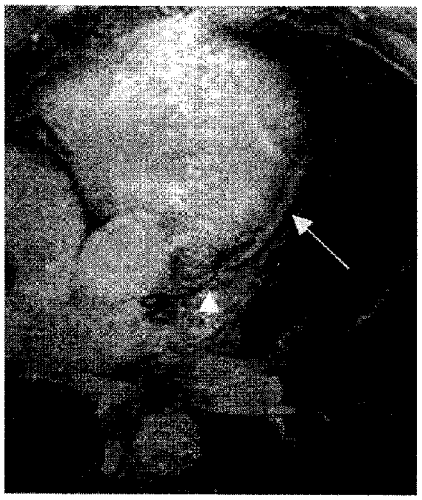 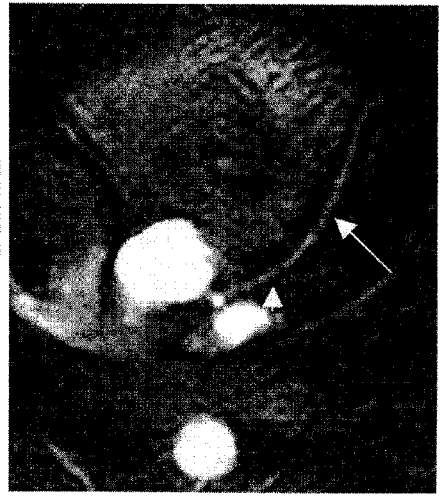

TIME RESOLVED CONTRAST-ENHANCED MR PROJECTION IMAGING OF THE CORONARY ARTERIES WITH INTRAVENOUS CONTRAST INJECTION

FEDERAL FUNDING LEGEND

This invention was produced in part using funds from the Federal government under NIH Grant Nos. HL38698 and HL70859. Accordingly, the Federal government has certain rights in this invention.

BACKGROUND OF THE INVENTION

1. Field of the Invention

The present invention relates to a method and apparatus for magnetic resonance imaging, and in particular to a method and apparatus for magnetic resonance imaging of the coronary arteries.

2. Description of the Prior Art

A study by Kim et al. entitled "Coronary Magnetic Resonance Angiography for the Detection of Coronary Stenoses," New England Journal of Medicine (2001), Vol. 345, No. 26, pages 1863-1869 showed that coronary artery magnetic resonance angiography (MRA) may be a viable diagnostic alternative to selective x-ray catheter-based angiography. The detection of coronary artery stenoses using MRA may be improved by viewing the entire artery as a whole, so as to prevent a torturous segment of the artery from mimicking a stenosis, and thus causing a misdiagnosis, as reported in "Whole-Heart Steady-State Free Precession Coronary Artery Magnetic Resonance Angiography," Weber et al., Magnetic Resonance in Medicine, Vol. 50 (2003), pages 1223-1228.

Coronary artery datasets often are evaluated either in cine mode or are reformatted using various image processing tools designed to remove the signal produced by adjacent tissue. Example of such techniques are described in "'Soap-Bubble' Visualization and Quantitative Analysis of 3D Coronary Magnetic Resonance Angiograms," Etienne et al., Magnetic Resonance in Medicine, Vol. 48, No. 4 (2002), pages 658-666 and "Coronary Artery Imaging Using Contrast-Enhanced 3D Segmented EPI," Deshpande et al., Journal of Magnetic Resonance Imaging, Vol. 13, No. 5 (2001), pages 676-681. Because of the strong signal produced by nearby cardiac chambers and the tortuous path of coronary arteries, such procedures can be time consuming, and there efficacy often is heavily dependent on user training. This is true even for contrast-enhanced 3D coronary MRA, when adjacent tissue often is dramatically suppressed by magnetization preparation, as described in "Coronary Arteries: Magnetization-Prepared Contrast-Enhanced Three-Dimensional Volume-Targeted Breath-Hold MR Angiography," Li et al., Radiology, Vol. 1019, No. 1 (2001), pages 270-277

SUMMARY OF THE INVENTION

It is an object of the present invention to provide a magnetic resonance imaging method and apparatus for depicting coronary arteries as a whole, substantially without a signal from adjoining tissue and cardiac chambers, wherein extensive post-processing of the image is not necessary.

It is a further object of the present invention to provide such a magnetic resonance imaging method and apparatus suitable for use in contrast-enhanced magnetic resonance angiography.

This object is achieved in accordance with the principles of the present invention in a magnetic resonance imaging method and apparatus wherein a thick two-dimensional projection is obtained for imaging the entire coronary artery in a single slice. A small amount of magnetic resonance contrast agent is injected into the subject prior to obtaining the projection, making the blood appear brighter in the magnetic resonance image. Because the injection is small and projection imaging is inherently faster than three-dimensional imaging, images of the coronary arteries can be obtained during the brief time period when the contrast agent is in the artery, but not in the cardiac chambers. Magnetic resonance data for the two-dimensional projection are obtained using a pulse sequence having special preparation radio-frequency (RF) pulses, which significantly reduce the image intensity of the myocardium and fat surrounding the coronary arteries. Therefore, the signal contribution (image intensity) from the myocardium and fat is small, but the contrast agent makes the image intensity for the coronary arteries high. Because the contrast between the vessel and the surrounding tissue is high, and because the entire coronary artery is within the single imaging slice, no imaging processing techniques are necessary.

DESCRIPTION OF THE DRAWINGS

FIG. 3a is a magnetic resonance image of the right coronary artery (RCA) before injection of a bolus of contrast agent, FIG. 3b shows the same imaged region after injection of the contrast agent bolus wherein the right ventricle and the pulmonary artery are enhanced, and FIG. 3c shows the same imaged region when the bolus first reaches the aorta, and has excited the right side of the heart, allowing a clear depiction of the RCA.

FIG. 4a shows a maximum intensity projection (MIP) of the RCA using a pre-contrast localizer scan, FIG. 4b shows a thick slice projection of the RCA following injection of contrast agent.

FIG. 5a shows a pre-contrast SFP localizer of the left anterior descending (LAD) coronary artery, wherein proximal portions of the artery remain obscured, and FIG. 5b shows a thick-slice projection image of the LAD following injection of a tight bolus of contrast agent in accordance with the invention.

DESCRIPTION OF THE PREFERRED EMBODIMENTS

Figure 6:
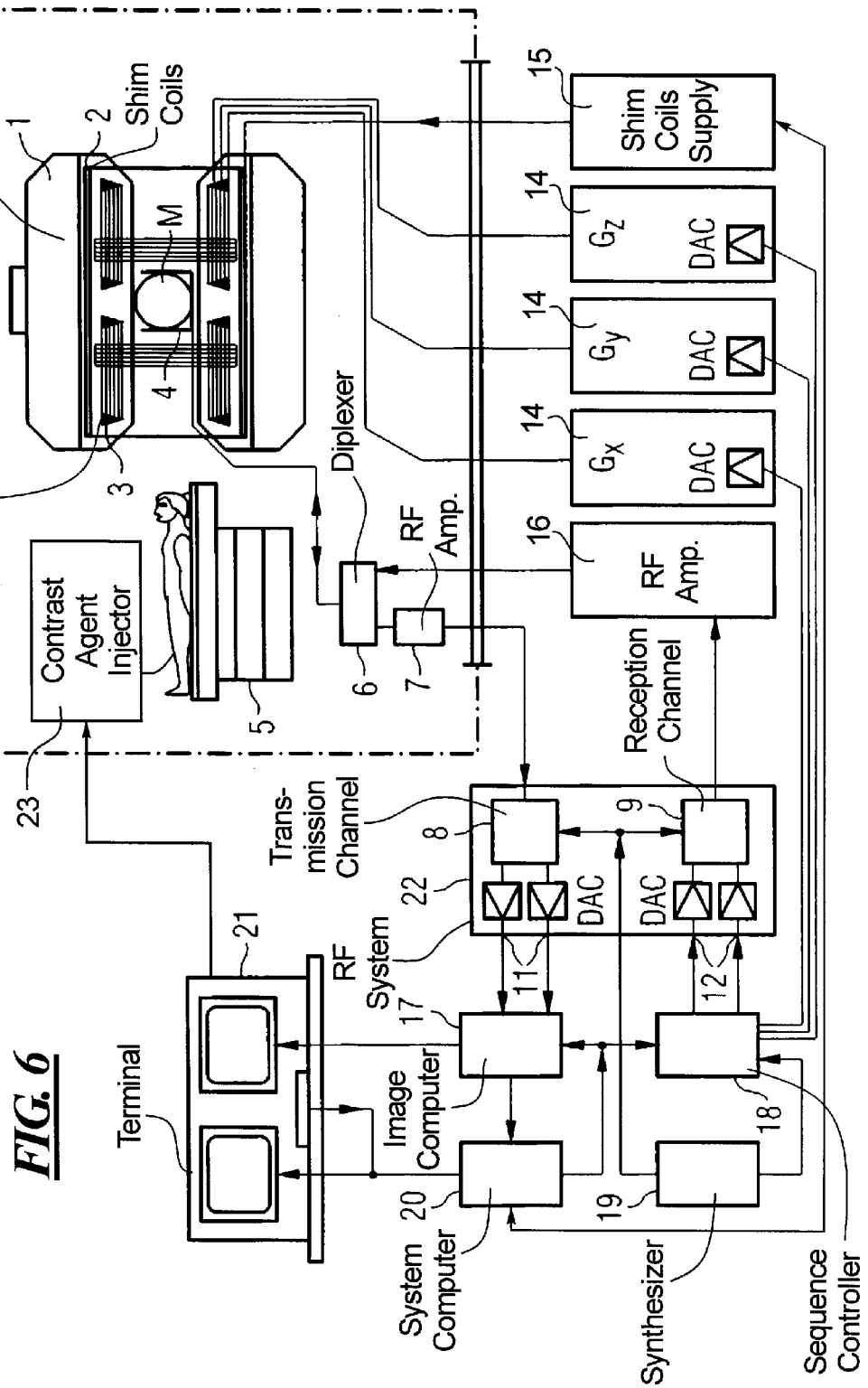
FIG. 6 is a block diagram of a magnetic resonance imaging apparatus constructed and operating in accordance with the principles of the present invention.

FIG. 6 schematically illustrates a magnetic resonance imaging (tomography) apparatus for generating a nuclear magnetic image of a subject according to the present invention. The components of the nuclear magnetic resonance tomography apparatus correspond to those of a conventional tomography apparatus, but it is controlled according to the invention. A basic field magnet 1 generates a time-constant, intense magnetic field for polarization (alignment) of the nuclear spins in the examination region of a subject such as, for example, a part of a human body to be examined. The high homogeneity of the basic magnetic field required for the nuclear magnetic resonance measurement is defined in a spherical measurement volume M in which the part of the human body to be examined is introduced. For supporting the homogeneity demands and, in particular, for eliminating time-invariable influences, shim plates of ferromagnetic material are attached at suitable locations. Time-variable influences are eliminated by shim coils 2 that are driven by a shim power supply 15.

A cylindrical gradient coil system 3 is built into the basic field magnet 1, the system 3 being composed of three sub-windings. Each sub-winding is supplied with current by an amplifier 14 for generating a linear gradient field in the respective directions of a Cartesian coordinate system. The first sub-winding of the gradient field system 3 generates a gradient Gx in the x-direction, the second sub-winding generates a gradient Gy in the y-direction, and the third sub-winding generates a gradient Gz in the z-direction. Each amplifier 14 has a digital-to-analog converter DAC that is driven by a sequence control 18 for the time-controlled generation of gradient pulses.

A radio-frequency antenna 4 is situated within the gradient field system 3. The antenna 4 converts the radio-frequency pulses emitted by a radio-frequency power amplifier into an alternating magnetic field for exciting the nuclei and aligning the nuclear spins of the subject under examination, or of a region of the subject under examination. The radio-frequency antenna 4 is composed of one or more RF transmission coils and a number of RF reception coils in the form of an arrangement (preferably linear) of component coils. The alternating field proceeding from the precessing nuclear spins, i.e. the nuclear spin echo signals produced as a rule by a pulse sequence composed of one or more radio-frequency pulses and one or more gradient pulses, is also converted into a voltage by the RF reception coils of the radio-frequency antenna 4, this voltage being supplied via an amplifier 7 to a radio-frequency reception channel 8 of a radio-frequency system 22. The radio-frequency system 22 also has a transmission channel 9 wherein the radio-frequency pulses are generated for exciting magnetic nuclear resonance. The respective radio-frequency pulses are digitally presented as a sequence of complex numbers on the basis of a pulse sequence in the sequence control 18 prescribed by the system computer 20. This number sequence—as a real part and an imaginary part—is supplied via respective inputs 12 to a digital-to-analog converter DAC in the radio-frequency system 22 and is supplied from there to a transmission channel 9. In the transmission channel 9, the pulse sequences are modulated onto a radio-frequency carrier signal having a basic frequency corresponding to the resonant frequency of the nuclear spins in the measurement volume.

The switching from transmission mode to reception mode ensues via a transmission/reception diplexer 6. The RF transmission coil of the radio-frequency antenna 4 radiates the radio-frequency pulses, based on signals from a radio-frequency amplifier 16, for excitation of the nuclear spins into the measurement volume M and samples the resulting echo signals via the RF reception coils. The acquired nuclear magnetic resonance signals are phase-sensitively demodulated in the reception channel 8 of the radio-frequency system 22 and are converted via respective analog-to-digital converters ADC into the real part and the imaginary part of the measured signal, which are respectively supplied to outputs 11. An image computer 17 reconstructs an image from the measured data acquired in this way. Administration of the measured data, the image data and the control programs ensues via the system computer 20. On the basis of control programs, the sequence control 18 monitors the generation of the respectively desired pulse sequences and the corresponding sampling of k-space. In particular, the sequence control 18 controls the tined switching of the gradients, the emission of the radio-frequency pulses with defined phase and amplitude, as well as the reception of the nuclear magnetic resonance signals. The timing signals for the radio-frequency system 22 and the sequence control 18 are made available by a synthesizer 19. The selection of corresponding control programs for generating a nuclear magnetic resonance image as well as the presentation of the generated nuclear magnetic resonance image ensues via a terminal 21 that has a keyboard as well as one or more picture screens.

Contrast agent is injected into the patient by a contrast agent injector 23, which can be individually controllable or controllable via the terminal 21.

The SSFP pulse sequence shown in FIG. 1, and described in more detail below, is implemented in the apparatus shown in FIG. 6 by the sequence control 18, upon being selected via the terminal 21. Manipulation of the acquired magnetic resonance data in accordance with the invention takes place in the image computer 12 in the apparatus shown in FIG. 6.

Figure 1:
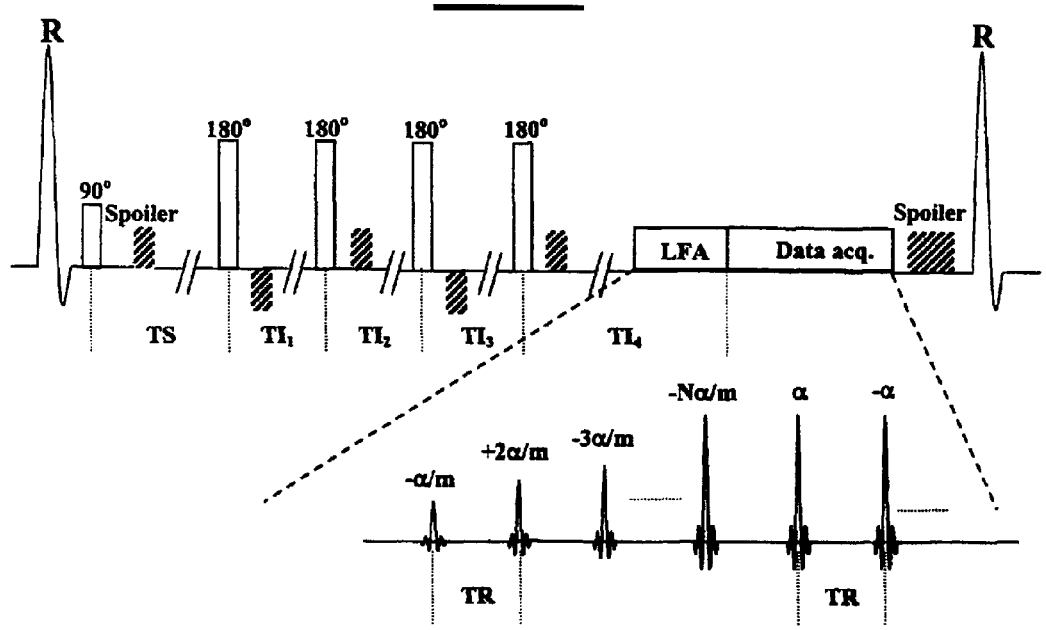
FIG. 1 illustrates a steady state-free precession (SSFP) pulse sequence with a multiple inversion pulse magnetization preparation, suitable for use in the inventive method and apparatus.

The inventive method employs an SSFP pulse sequence with a multiple inversion pulse magnetization preparation, as shown in FIG. 1. Because of the short period of RCA enhancement following injection of a small contrast agent bolus, a 2D thick-slice projection imaging sequence is employed to obtain sufficient coverage, while keeping the acquisition time short. Magnetization preparation is employed to keep the signal from background tissues (i.e., myocardium, fat) that is present in the thick 2D slice from obscuring the RCA.

The magnetization preparation technique embodied in the inventive method has been previously demonstrated to effectively suppress background tissue diagnostic angiography, as reported in "Background Suppression with Multiple Inversion Recovery Nulling: Applications to Projective Angiography," Mani, Magnetic Resonance in Medicine, Vol. 37, No. 6 (1997), pages 898-905.

After detection of the R-wave, a 90° saturation pulse is applied, followed by a saturation time TS. This is followed by a train of four 180° inversion pulses, separated by delay times $TI_1$, $TI_2$, $TI_3$ and $TI_4$. Linear flip angle (LFA) preparation pulses are applied at the end of $TI_4$. TS and $TI_1$ through $TI_4$ need not necessarily be equal. In the embodiment shown in FIG. 1, five LPA preparation pulses were applied during $TI_4$ immediately before data acquisition, for reducing signal oscillations during data acquisition and associated ghosting artifacts.

Figure 2:
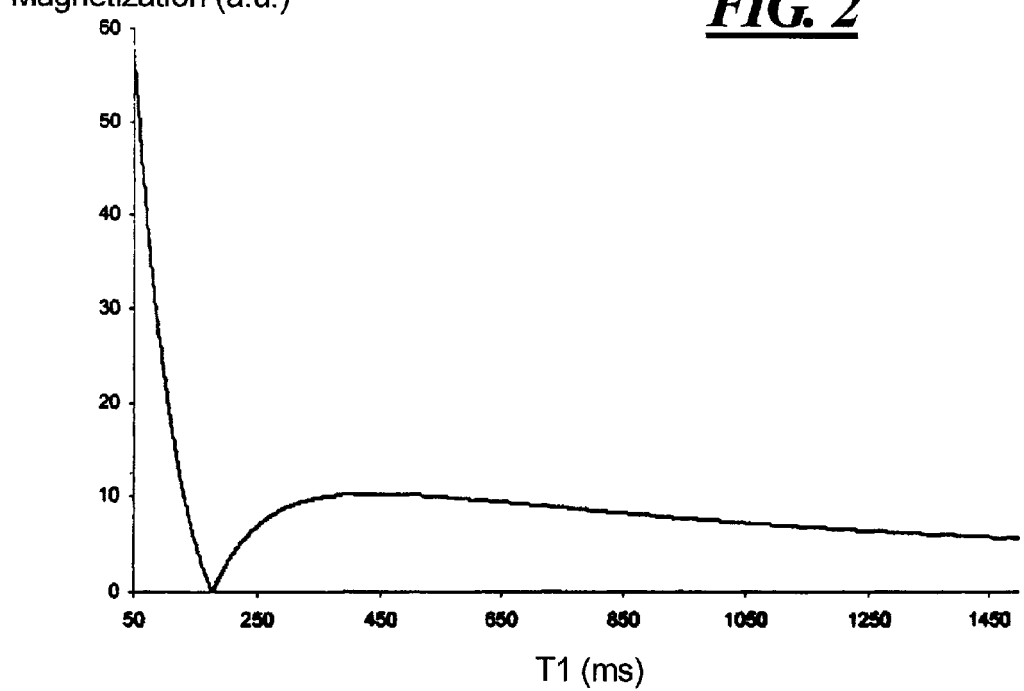
FIG. 2 shows the longitudinal magnetization at the start of data acquisition over a range of T1 values for the magnetization prepared SSFP sequence shown in FIG. 1.

FIG. 2 shows the longitudinal magnetization at the start of data acquisition over a range of T1 values (50 ms through 1500 ms) for the magnetization prepared SSFP sequence shown in FIG. 1. The longitudinal magnetization is high (greater than 50% of its equilibrium value) for contrast enhanced blood (T1=50 ms) but is less than 11% of its equilibrium value for tissue types with T1>250 ms a.u.=arbitrary units.

When a bolus of gadolinium-based (Gd) contrast agent is injected intravenously in a healthy patient, there is a time delay of approximately five seconds between enhancement of blood in the right cardiac chambers and enhancement of the right coronary artery (RCA), as reported in "Analysis of Cardiopulmonary Transmit Times at Contrast Material-Enhanced MR Imaging in Patients with Heart Disease," Francois et al., Radiology, Vol. 227 (2003), pages 447-452. In accordance with the invention, if a small enough bolus is injected, there will be a short window of time when first-pass Gd will have washed out of the right heart chambers, but the RCA still will be enhanced. With a rapid imaging sequence in accordance with the invention, this window is sufficient to acquire images of the RCA.

Studies were conducted in six healthy volunteers (4 male, 2 female, mean age=41 years, range=24-57 years of age) on a Siemens Sonata 1.5T Scanner, generally corresponding to the apparatus illustrated in FIG. 6. The studies were conducted using a maximum gradient amplitude of 40 mT/m and slew rate of 200 mT/m/ms. The volunteers were required to hold their breath during scanning, an electrocardiographic triggering was used to minimize the effect of physiological motion. For each volunteer, three-dimensional SSFP localizer scans were employed to locate the approximate orientation of the RCA. Once localization was complete, an automated injection system (Spectris, available from Medrad, Indianola, Pa.), schematically indicated by the contrast agent injector 23 in FIG. 6, to administer a small IV injection (8 mL, rate=4 mL/s) of Gd contrast agent (Magnevist, available from Berlex Laboratories, Wayne, N.J.). This was followed by an IV injection of saline (12-16 mL, rate=4 mL/s). The RCA was scanned using the predetermined RCA localization with the magnetization prepared, segmented, thick-slice 2D SSFP sequence shown in FIG. 1.

A sliding window reconstruction technique was used so that a new image was reconstructed using data collected during the three most recent heartbeats. Typical imaging parameters were: TR (repetition time)/TE (echo time)/flip angle=3.7 ms/1.6 ms/70°; FOV (field of view)=150×300 mm$^2$, acquisition matrix=105×256 (phase-encoding×readout); in-plane spatial resolution=1.4×1.2 mm$^2$; centric ordering in the phase-encoding direction, imaging bandwidth=400 Hz/pixel; 35 lines/segment; slice thickness=2 cm. Asymmetric sampling was used in the readout direction to reduce TR. To determine the appropriate values for Ts, $TI_1$, $TI_2$, $TI_3$ and $TI_4$, a simulation of the sequence was preformed using the Bloch equations in MatLab®. The simulation showed that Ts=25 ms. $TI_1$=75 ms, $TI_2$=15 ms, $TI_3$=190 ms and $TI_4$=95 ms resulted in uniform suppression of a wide range of background tissues, such as myocardium (T1=900 ms) and fat (T1=250 ms), while maintaining the high contrast-enhanced blood signal (T1=50 ms), as indicated in FIG. 2.

In one volunteer, the left anterior descending (LAD) coronary artery was localized and scanned using thick-slice projection SSFP to assess the effectiveness of the inventive method for depicting the left coronary arteries. Injection and imaging parameters were identical to those described above for RCA projection imaging, with the exception that the slice thickness was decreased to 10 mm to reduce the signal contribution of contrast-enhanced blood in the left cardiac chambers following the small bolus injection.

To assess the effectiveness of the inventive method, the signal-to-noise ratio (SNR), the contrast-to-noise ratio (CNR) and the vessel length were calculated for each contrast-enhanced image. Source images were used for all measurements. To measure SNR and CNR, regions-of-interest (ROI) were drawn in intermediate portions of the RCA for each volunteer. ROIs were also drawn in background tissue adjacent to the vessel ROI and in air. The SNR was calculated by dividing the vessel signal by an air signal and multiplying by ½5, a technique described in "Measurement of Signal Intensities in the Presence of Noise in MR Images," Henkelman, Medical Physics, Vol. 12, No. 2 (1985), pages 232-233. The vessel length was measured by drawing line segments along the course of the artery and summing the length of all of the segments. These values are discussed below as mean±standard error.

In all volunteers, the RCA was visualized following a small injection of Gd using thick-slice magnetization prepared SSFP. Because a small (8 mL) bolus of contrast agent was injected, Gd enhancement was localized to specific regions of the heart during the time course of the contrast agent injection. With a new image reconstructed every heartbeat using the sliding window reconstruction technique, it was possible to monitor the contrast bolus as it entered the right atrium (RA), the right ventricle (RV), the pulmonary artery (PA) and finally the RCA. FIG. 3a shows the image before injection, wherein the image is mostly dark. FIG. 3b shows the situation following IV injection of a tight Gd bolus, wherein the contrast agent enhances the RV and the PA. FIG. 3c shows the situation when the first pass Gd reaches the aorta and has thus exited the right side of the heart, allowing a clear depiction of the RCA, as indicated by the arrows. The magnetization preparation successfully suppressed the blood signal from adjacent cardiac chambers. Segment of the RCA which were obscured in the pre-contrast localizer were visible following the small bolus contrast injection. FIG. 4a shows a maximum intensity projection (MIP) of the RCA, using the pre-contrast localizer scan.

FIG. 4b shows the thick-slice projection of the RCA following the injection of contrast agent, wherein it can be seen that distal portions of the RCA, by the arrowhead, are obscured by background tissue in FIG. 4a, but are clearly depicted in FIG. 4b.

Distal branching of the RCA, which was not visible in the localizer scans, was visible in the contrast-enhanced scans in 50% of the volunteers in the study.

In each volunteer, at least 5 cm of the RCA was visible. The mean visualized length of the RCA was 7.1±0.9 cm. The mean SNR was 11.8±0.7. The mean CNR was 6.1±0.6. In one volunteer, projection SSFP was used to visualize the LAD. FIG. 5a shows the pre-contrast SSFP localizer of the LAD, indicated by the arrow, wherein it can be seen that proximal portions of the artery by the arrowhead remain obscured. FIG. 5b shows a thick-slice projection imaging of the LAD following injection of a tight bolus of Gd. Although the slice thickness was reduced to 10 mm to minimize the enhanced blood in the left cardiac chambers from overlapping the LAD, 7.26 cm of the vessel is still visible, and the proximal and more distal portions of the artery are visible as well.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for contrast-enhanced magnetic resonance (MR) angiography of the right coronary artery of a patient, comprising the steps of:

selecting a bolus of MR contrast agent of a size causing said bolus, after injection into a patient, to wash out of right coronary chambers of the heart while still enhancing MR signals from the right coronary artery;

injecting said bolus into the patient;

generating MR signals in and obtaining MR signals from the patient, sufficient only for generating one 2D projection image in a single slice, in a time window after said bolus has washed out of the right coronary chambers and still enhances MR signals in the right coronary artery; and generating only one 2D projection MR image of the right coronary artery in said single slice using only the MR signals obtained in said time window.

2. A method as claimed in claim 1 wherein the step of generating MR signals in and obtaining MR signals from the patient in said time window comprises generating said MR signals in and obtaining said MR signals from the patient in said time window using 2D thick-slice projection imaging.

3. A method as claimed in claim 2 wherein the step of using 2D thick-slice projection imaging comprises using 2D thick-slice magnetization prepared projection imaging.

4. A method as claimed in claim 3 wherein the step of using 2D thick-slice magnetization prepared projection imaging comprises using 2D thick-slice magnetization prepared steady state free precession imaging.

5. A method as claimed in claim 4 wherein the step of using 2D thick-slice magnetization prepared steady state free precessing imaging comprises emitting a 90° saturation pulse followed by a time delay, followed by a train of four 180° inversion pulses, each separated by respective inversion times.

6. A method as claimed in claim 5 comprising employing 25 ms as said time delay.

7. A method as claimed in claim 5 comprising employing 75 ms as a first of said inversion times, 15 ms as a second of said inversion times, 190 ms as a third of said inversion times, and 95 ms as a fourth of said inversion times.

8. A method as claimed in claim 1 wherein the step of generating MR signals in and obtaining MR signals from the patient in a time window comprises generating said MR signals in and obtaining said MR signals from the patient in a time window consisting of three heartbeats of the patient.

9. A method as claimed in claim 1 comprising selecting said size of said bolus to be 8 mL, and injecting said bolus into the patient at an injection rate of 4 mL/s.

10. A method as claimed in claim 1 comprising, prior to injecting said bolus into the patient, conducting an MR localization scan of the patient for locating an approximate orientation of the right coronary artery in the patient, and generating said MR signals in and obtaining said MR signals from the patient in said time window dependent on said orientation.

11. An apparatus for contrast-enhanced magnetic resonance (MR) angiography of the right coronary artery of a patient, comprising:

a contrast agent injector configured to interact with a patient that injects a bolus of MR contrast agent into the patient, said bolus having a size causing said bolus, after injection into a patient, to wash out of right coronary chambers of the heart while still enhancing MR signals from the right coronary artery;

an MR scanner configured to interact with the patient that generates MR signals in and that obtains MR signals from the patient;

a sequence controller that operates said scanner with a pulse sequence to obtain said MR signals from the patient, sufficient only for generating only one 2D projection image in a single slice, in a time window after said bolus has washed out of the right coronary chambers and still enhances MR signals in the right coronary artery; and an image computer supplied with said MR signals that generates only one 2D projection MR image of the right coronary artery in said single slice using only the MR signals obtained in said time window.

12. An apparatus as claimed in claim 11 wherein said sequence controller operates said MR scanner to obtain said MR signals from the patient in said time window using a pulse sequence for 2D thick-slice projection imaging.

13. An apparatus as claimed in claim 12 wherein said sequence controller operates said MR scanner using a pulse sequence for 2D thick-slice magnetization prepared projection imaging.

14. An apparatus as claimed in claim 13 wherein said sequence controller operates said MR scanner using a pulse sequence for 2D thick-slice magnetization prepared steady state free precession imaging.

15. An apparatus as claimed in claim 11 wherein said sequence controller operates said MR scanner using a 2D thick-slice magnetization prepared steady state free precessing imaging comprising a 90° saturation pulse followed by a time delay, followed by a train of four 180° inversion pulses, each separated by respective inversion times.

16. An apparatus as claimed in claim 15 wherein said sequence controller employs 25 ms as said time delay in said pulse sequence.

17. An apparatus as claimed in claim 15 wherein said sequence controller employs 75 ms as a first of said inversion times, 15 ms as a second of said inversion times, 190 ms as a third of said inversion times, and 95 ms as a fourth of said inversion times in said pulse sequence.

18. An apparatus as claimed in claim 11 wherein said sequence controller operates said MR scanner to obtain said MR signals from the patient in a time window consisting of three heartbeats of the patient.

19. An apparatus as claimed in claim 11 wherein said contrast agent injector sets said size of said bolus to be 8 mL, and injects said bolus into the patient at an injection rate of 4 mL/s.

20. An apparatus as claimed in claim 11 wherein said sequence controller, prior to injection of said bolus into the patient, operates said MR scanner to conduct an MR localization scan of the patient to locate an approximate orientation of the right coronary artery in the patient, and wherein said image computer generates said MR signals in and obtains said MR signals from the patient in said time window dependent on said orientation.

* * * * *